(12) United States Patent
Alberts et al.

(10) Patent No.: US 10,667,682 B2
(45) Date of Patent: *Jun. 2, 2020

(54) ASSESSMENT OF LOW CONTRAST VISUAL SENSITIVITY

(71) Applicant: THE CLEVELAND CLINIC FOUNDATION, Cleveland, OH (US)

(72) Inventors: Jay L. Alberts, Chagrin Falls, OH (US); Robert Bermel, Cleveland Hts., OH (US); Stephen Rao, Chagrin Falls, OH (US); David D. Schindler, Russell, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/041,947

(22) Filed: Jul. 23, 2018

(65) Prior Publication Data

US 2018/0325370 A1 Nov. 15, 2018

Related U.S. Application Data

(63) Continuation of application No. 15/131,645, filed on Apr. 18, 2016, now Pat. No. 10,028,653.

(Continued)

(51) Int. Cl.
| | | |
|---|---|---|
| *A61B 3/032* | (2006.01) | |
| *A61B 3/00* | (2006.01) | |
| *A61B 3/02* | (2006.01) | |
| *A61B 3/06* | (2006.01) | |
| *A61B 5/00* | (2006.01) | |

(52) U.S. Cl.
CPC .......... *A61B 3/032* (2013.01); *A61B 3/0025* (2013.01); *A61B 3/0033* (2013.01); *A61B 3/0058* (2013.01); *A61B 3/022* (2013.01); *A61B 3/063* (2013.01); *A61B 5/0022* (2013.01); *A61B 5/7435* (2013.01)

(58) Field of Classification Search
CPC ....... A61B 3/022; A61B 3/032; A61B 3/0033; A61B 3/0041; A61B 3/0058; A61B 3/063; A61B 3/0025
USPC .................. 351/223, 237, 239, 246
See application file for complete search history.

(56) References Cited

U.S. PATENT DOCUMENTS

| | | |
|---|---|---|
| 4,861,156 A | 8/1989 | Terry |
| 6,293,675 B1 | 9/2001 | Eger |

(Continued)

FOREIGN PATENT DOCUMENTS

| | | |
|---|---|---|
| GB | 2514529 A | 12/2014 |
| WO | 2013/170091 A1 | 11/2013 |

OTHER PUBLICATIONS

PCT International Search Report and Written Opinion for International Application Serial No. PCT/US2016/028087, dated Jul. 14, 2016, pp. 1-12.

*Primary Examiner* — Jordan M Schwartz
(74) *Attorney, Agent, or Firm* — Tarolli, Sundheim, Covell & Tummino LLP

(57) ABSTRACT

Devices, systems and methods are described that can facilitate automated administration of a low contrast visual acuity test to a user. The low contrast visual acuity test can be administered using a display device and a computing device. The computing device can score results of the low contrast visual acuity test and determine a visual status of the user based on the score.

20 Claims, 8 Drawing Sheets

Related U.S. Application Data

(60) Provisional application No. 62/149,380, filed on Apr. 17, 2015.

(56) References Cited

U.S. PATENT DOCUMENTS

| | | | |
|---|---|---|---|
| 10,028,653 B2 * | 7/2018 | Alberts | A61B 3/0025 |
| 2004/0058015 A1 | 3/2004 | Tao | |
| 2004/0141152 A1 | 7/2004 | Marino et al. | |
| 2006/0114414 A1 | 6/2006 | McGrath et al. | |
| 2011/0085140 A1 | 4/2011 | Brown et al. | |
| 2012/0050685 A1 | 3/2012 | Bartlett et al. | |
| 2012/0092622 A1 | 4/2012 | Hirayama | |
| 2012/0249951 A1 | 10/2012 | Hirayama | |
| 2012/0287163 A1 * | 11/2012 | Djavaherian | G09G 5/00 345/667 |
| 2013/0128229 A1 | 5/2013 | Huang | |
| 2013/0141697 A1 | 6/2013 | Berry et al. | |
| 2013/0301007 A1 * | 11/2013 | Wolffsohn | A61B 3/032 351/239 |
| 2015/0134346 A1 | 5/2015 | Hyde et al. | |
| 2015/0150444 A1 | 6/2015 | Bex et al. | |
| 2016/0078594 A1 | 3/2016 | Scherlen | |
| 2016/0220162 A1 * | 8/2016 | Mantysalo | A61B 3/0091 |
| 2017/0135571 A1 | 5/2017 | Schubart et al. | |
| 2017/0181617 A1 | 6/2017 | Bonnin et al. | |

* cited by examiner

ASSESSMENT OF LOW CONTRAST VISUAL SENSITIVITY

RELATED APPLICATIONS

This application is a continuation of U.S. application Ser. No. 15/131,645, filed Apr. 18, 2016, entitled "ASSESSMENT OF LOW CONTRAST VISUAL SENSITIVITY," which claims the benefit of U.S. Provisional Application No. 62/149,380, filed Apr. 17, 2015, entitled "ASSESSMENT OF LOW CONTRAST VISUAL SENSITIVITY." The entirety of each of the above-identified applications is hereby incorporated by reference for all purposes.

TECHNICAL FIELD

This disclosure relates generally to devices, systems and methods to assess low contrast visual sensitivity using a mobile computing device.

BACKGROUND

Various neurological diseases manifest themselves in a deterioration of visual function. Although basic black-on-white visual acuity is often documented as part of a basic neurological exam, contrast sensitivity is rarely evaluated comprehensively. However, in some populations (e.g., including users with multiple sclerosis (MS), Parkinson's disease (PD), traumatic brain injury (TBI), etc.), contrast sensitivity is the more sensitive measure when compared against black-on-white visual acuity. Current standard clinical assessments of contrast sensitivity are limited to pocket- or wall-based charts utilizing optotypes of varying size and contrast. While these standard clinical assessments have clinical utility, they suffer from various limitations (e.g., required to be administered by a technician, limited when used to study pure contrast sensitivity, etc.).

SUMMARY

In some aspects, the disclosure relates to a system to assess low contrast visual sensitivity of a user. The system includes a display device, a sensor to measure a property related to a distance between the display device and the user, and the computing device. The computing device comprising a memory storing computer-executable instructions; and a processor to execute the computer-executable instructions. Upon execution, the computer-executable instructions can at least: launch at least one module related to a low contrast visual acuity test; display a graphical user interface (GUI) on the display device, wherein the GUI corresponds to the low contrast visual acuity test; calculate the distance between the display device and the user based on the property; when the distance between the display device and the user is within a test value, administer the low contrast visual acuity test to the user using the GUI by executing the at least one module to present a series of images to a user; receive inputs from the user via the GUI based on the series of images being presented to the user; determine a score for the user based on a number of inputs comprising acceptable (or correct) answers that are within a normal range; and determine a visual status of the user based on the score.

In some aspects, the disclosure relates to a method to assess low contrast visual sensitivity of a user. The method can be executed by a computing device comprising a processor. The method can include: launching at least one module related to a low contrast visual acuity test; displaying a graphical user interface (GUI) on a display device, wherein the GUI corresponds to the low contrast visual acuity test; calculating, a distance between the display device and a user based on data related to the distance measured by a sensor; when the distance between the display device and the user is within a test value, administering the low contrast visual acuity test to the user using the GUI by executing the at least one module to present a series of images to a user; receiving inputs from the user via the GUI based on the series of images being presented to the user; determining a score for the user based on a number of inputs comprising acceptable (or correct) answers that are within a normal range; and determining a visual status of the user based on the score.

DETAILED DESCRIPTION

This disclosure relates to a system and method for performing an automated low contrast visual acuity test. For example, the low contrast visual acuity test can be performed on a computing device, which allows the user to perform the test without the need for a skilled human administrator of the test (e.g., a medical professional, a technician, an expert, or the like), which can lead to an increase in clinical utilization. Results of the low contrast visual acuity test can be utilized as part of a screening process to evaluate neurological conditions, such as: multiple sclerosis, Parkinson's disease, traumatic brain injury, and the like.

This disclosure describes two different tests that can be self-administered by a user: a low contrast letter acuity test and a contrast sensitivity vision test. The low contrast letter acuity test (LCLAT) can present optotypes at various contrasts and sizes and asks the user to respond, allowing self-testing at a range from the display. The contrast sensitivity vision test (CSVT) can provide an alternate method for measuring contrast sensitivity through the measurement of a contrast sensitivity function (CSF) that utilizes sinusoidal gratings of varying spatial frequency and contrast levels.

Figure 1:
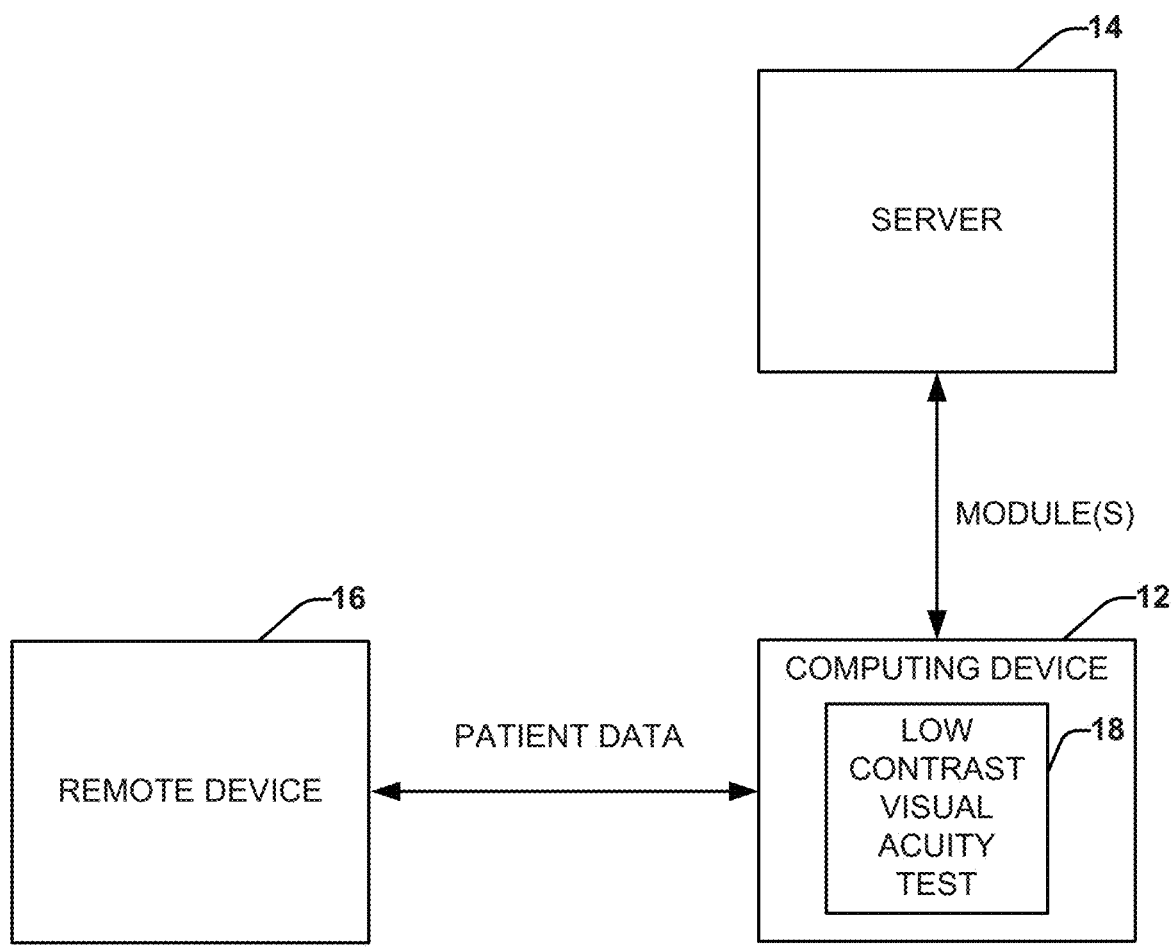
FIG. 1 depicts a block diagram of an example system that can facilitate the administration of an automated low contrast visual acuity test to a user.

FIG. 1 depicts an example system that can facilitate the administration of an automated low contrast visual acuity test 18 to a user. The low contrast visual acuity test 18 can be administered to the user using a computing device 22. For example, the computing device can be a mobile computing device, such as a smartphone, a tablet computer, a laptop computer, or the like. The computing device 22 removes the requirement for a skilled human administrator (e.g., a medical professional, a technician, an expert, or the like) to conduct the test.

The low contrast visual acuity test 18 can be implemented by the execution of one or more modules. A module, as used herein, is an encapsulation of code and data to implement a particular functionality. For example, a module can contain a plurality of images that can be used to conduct the low contrast visual acuity test. The module can also contain a correct answer corresponding to each of the plurality of images. At least one of the modules can be retrieved from a remote server 14. For example, the server can be located within the cloud to facilitate a cloud computing application. In some examples, the modules can be retrieved from two or more remote servers. As another example, the modules can be executed on the server 14. Based on the execution of the low contrast visual acuity test 18, the computing device 22 can send user data that includes results of the low contrast visual acuity test to a remote device 16 (e.g., a remotely located computing device) for further actions to be taken. The remote device 16 can belong to the user's doctor, for example.

Figure 2:
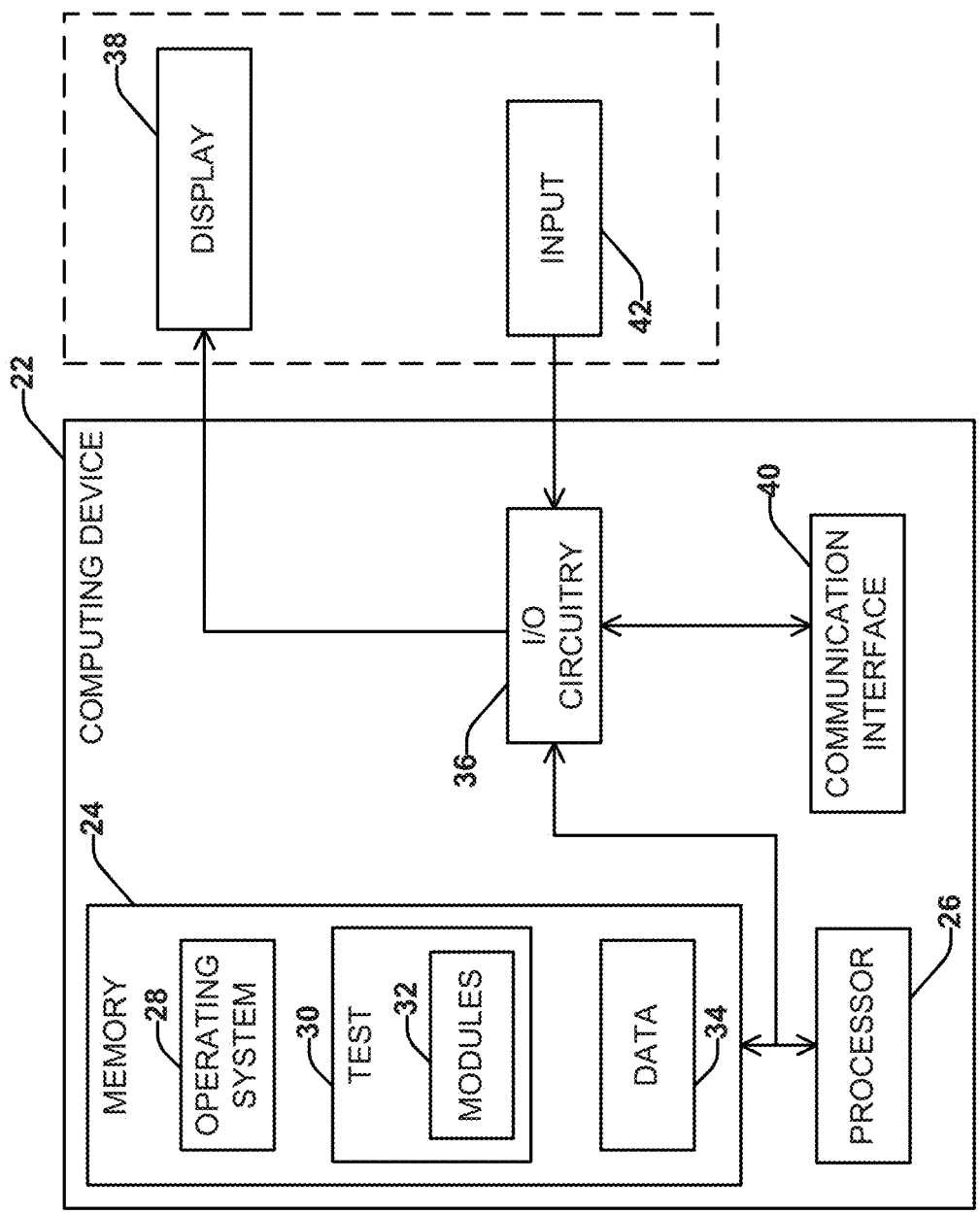
FIG. 2 depicts a block diagram of an example computing device that can administer the automated low contrast visual acuity test to the user.

FIG. 2 depicts an example computing device 22 configured to administer an automated low contrast visual acuity test to a user (or a plurality of users). The computing device 22 can include, or be coupled to, an input device 42 (or a set of one or more input devices) and a display device 38. The input device 42 and the display device 38 are each communicatively coupled to the computing device 22 (e.g., via I/O circuitry 36). In some examples, the display device 38 and the input device 42 can be part of the same device (e.g., a touch screen device). Although the input device 42 and the display device 38 are illustrated as separate from the computing device 22, one or both of the input device 42 and the display device 38 can be included within the computing device 22.

The computing device 22 can include one or more computing apparatuses that can include a memory 24 and a processor 26. The memory 24 can be a non-transitory memory that can be configured store machine readable instructions and data 34. By way of example, the memory 24 can store a variety of machine readable instructions and data 34, including an operating system 28, one or more application programs (including application programs for the test 30, including one or more program modules 32), and data 34, including test data, program data, and/or other data. The operating system 28 can be any suitable operating system or combinations of operating systems, which can depend on manufacturer and system to system corresponding to different computer manufacturers. The test data can be real time data acquired for an ongoing low contrast visual acuity test (e.g., the data is buffered in random access memory) or the test data can be previously acquired data. The other data can include image data or distance data acquired from one or more digital cameras or other distance sensors (e.g., to determine closeness to the screen for processing of results of the low contrast visual acuity test), demographic or personal information about the user for which the other device data has been acquired. For example, the other data can be input into the computing device 22 or can be acquired for the user, such as from an electronic health record or other database that may contain information about the respective user.

The memory 24 can be implemented, for example as volatile memory (e.g., RAM), nonvolatile memory (e.g., a hard disk, flash memory, a solid state drive or the like) or combination of both. It is to be understood that the memory 24 does not require a single fixed memory but the memory can include one or more non-transitory machine readable memory (e.g., volatile and/or non-volatile memory devices) that can store data and instructions. The memory 24 can store data 34 and/or instructions corresponding to the operating system 28 and/or the application in a single device or distributed across multiple devices, such as in a network or a cloud computing architecture.

As an example, the instructions can be stored and executed on a server (e.g., a web server) and accessed at another remote device (e.g., a computing device) for user interaction, such as via a web browser or other interface that is programmed to interact with the user interface that is generated. In some cases, the functionality can be distributed between the server and the remote device in which certain instructions are executed by the remote device and other instructions are executed by the server. In other examples, the instructions and data can be stored and executed locally in a computing device (e.g., a portable or mobile device), such as a tablet computer.

The processor 26 can be configured to access the memory 24 and execute the machine readable instructions to facilitate the performance of operations (e.g., corresponding to the operating system 28 and/or the application 30). For example, the processor 26 can be configured to access the memory 24 to access the application program 30 and/or the associated program modules 32 to implement the functions of the computing device 22 with regard to the analysis of the low contrast visual acuity. The application programs 30, associated program modules 32, and data 34 (including test data acquired by input device 42) can cooperate to analyze the low contrast visual acuity of the user.

In some examples, the computing device 22 can be implemented as a stationary personal computer or workstation. In other examples, the computing device 22 can be implemented as a portable computer, such as a notebook computer, a tablet computer or smart phone. The computing device 22 can include or be communicatively coupled via I/O circuitry 36 and a communication interface 40 (which can be either internal to the computing device 22 or external to the computing device) to an display device 38 (e.g., display/touchscreen) that provides a human-machine interface (HMI) that a user can employ to interact with the computing device 22. As used herein a user can refer to a person who uses the computing device 22. The user can be, for example, a test administrator, a doctor, a nurse, a patient, a researcher, or the like. However, in another example, the user can be a person other than an expert test administrator. As used herein a user can refer to a living subject (e.g., adult or child) in need of treatment by a physician, physician assistant, advanced practice registered nurse, veterinarian, or other health care provider or the subject may be a healthy subject that is to be tested for other reasons.

For example, the communication interface 40 can include a network interface that is configured to provide for communication with a corresponding network, such as can include a local area network or a wide access network (WAN) (e.g., the internet or a private WAN) or a combination thereof. As a further example, the communication interface 40 can send data 34 (e.g., test data and/or analysis data derived from test data) to a remote database. For instance, the computing device 22 can be programmed to upload and transfer such data to a remote database including an electronic health record (EHR) for the user. Such transfer of data can be HIPAA compliant and provided over a secure tunnel (e.g., HTTPS or the like). The transfer of test data and/or analysis data can be automated to occur upon completion of one or more balance tests. The data 34 provided by the computing device 22 can further be analyzed by an external analysis system or accessible remotely by an authorized user, such as a health care provider (e.g., a physician) or researcher for further analysis.

Figure 3:
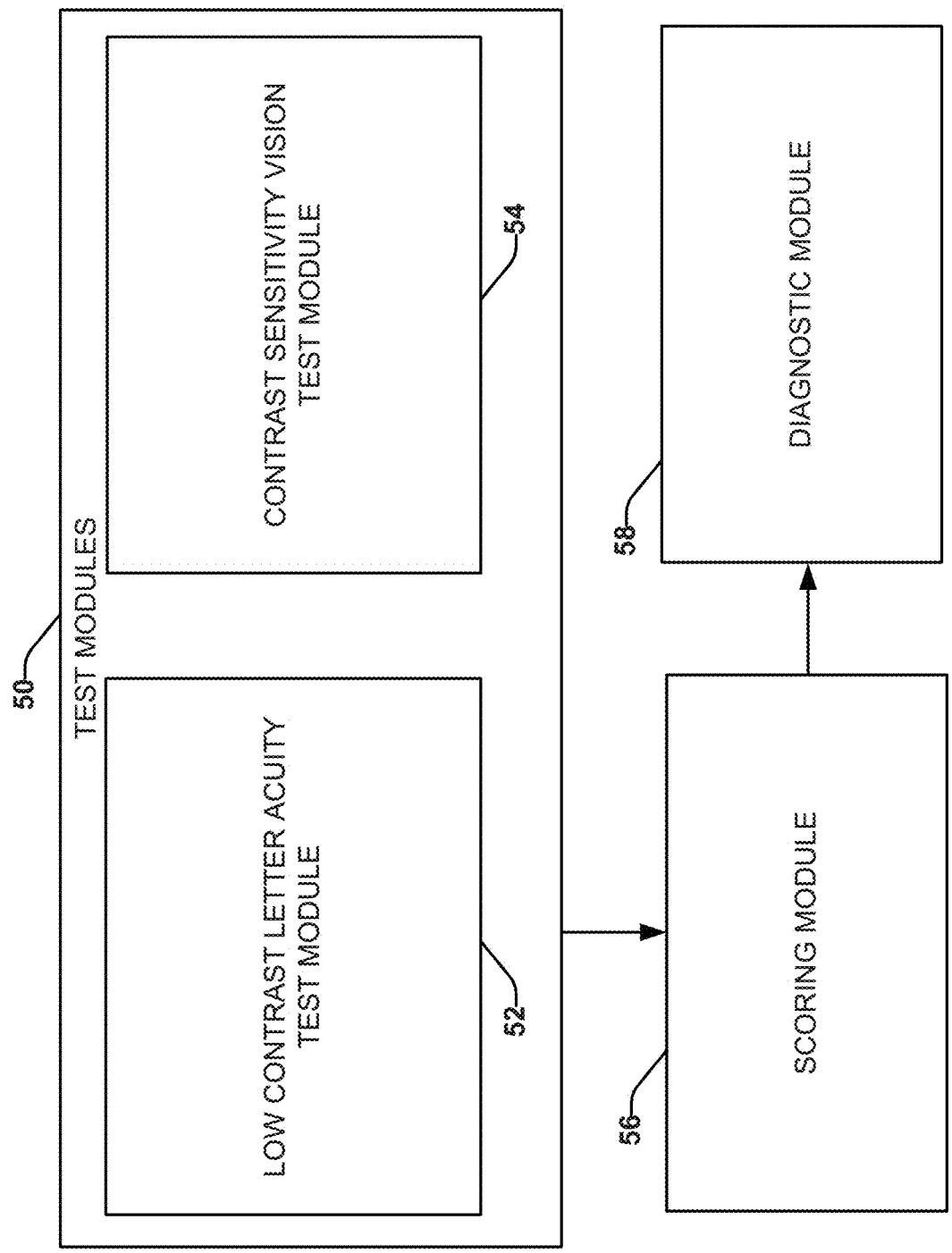
FIG. 3 depicts a block diagram of showing examples of various modules that can be utilized to conduct the automated low contrast visual acuity test.

For example, the data 34 provided by the computing device 22 can correspond to data representing results of a low contrast visual acuity test application 30. As shown in FIG. 3, the application includes test modules 50 that can facilitate performance of the low contrast visual acuity test. One or more of the test modules 50 can automate the administration of the low contrast visual acuity test (e.g., to increase clinical utilization), including a low contrast letter acuity test module 52 and/or a contrast sensitivity vision test module 54. In some instances, the low contrast letter acuity test module 52 and/or the contrast sensitivity vision test module 54 can be a mobile application (e.g., for implementation on a tablet computing device and/or a smartphone device). For example, one or more of the modules can be downloaded from a server within the cloud.

Figure 4:
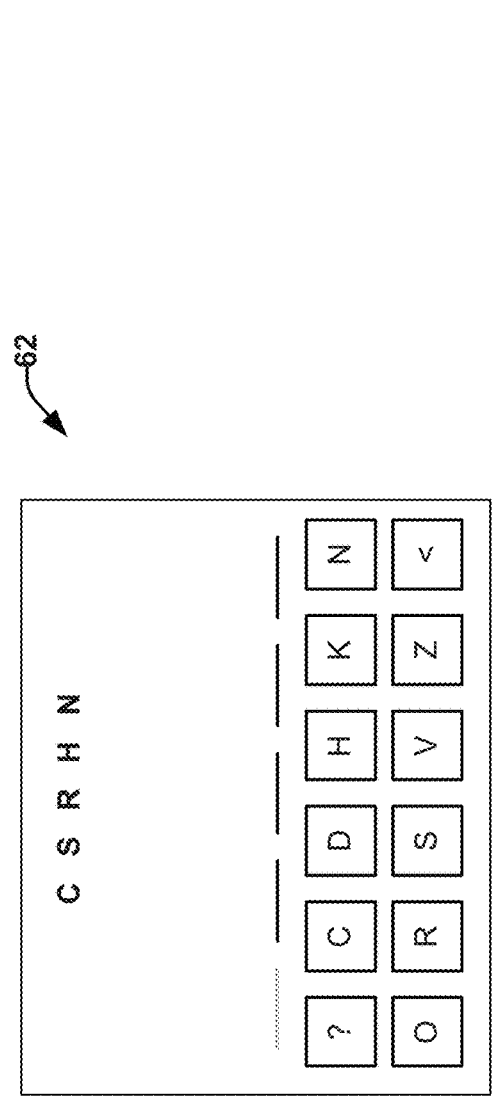
FIGS. 4 and 5 depict examples of images that can be generated to conduct the automated low contrast visual acuity test.

The low contrast letter acuity test module 52 can be used to administer a Low Contrast Letter Acuity Test (LCLAT). The low contrast letter acuity test module 52 can include a graphical user interface (GUI) that can present optotypes of various contrasts and sizes and ask the user to respond from an input such as a custom built on-screen keyboard, allowing the test to be self-administered by the user. An example of the GUI for the LCLAT test generated on a display device upon execution of the low contrast letter acuity test module 52 is shown in FIG. 4. As an example, the optotypes can employ predetermined coloring and/or shading. In a corresponding grayscale version, for example, the shading is applied via dithering to produce sine-wave grated patterns. As an alternative, without shading, the system would produce square-wave grated patterns—having different characteristics. Additionally or alternatively, in some examples, the test is implemented using shades of black and white. In other examples, such as for certain disease populations, color tests can be implemented.

Traditional LCLAT tests are administered with the user located 152 cm from the testing device. In contrast, the LCLAT test of the low contrast letter acuity test module 52 can enable the user to be a shorter distance from the display device. For example, the distance can be between 40 cm and 75 cm from the display device. In another example, the distance can be between 48 cm and 55 cm. In yet another example, the distance can be between 49 and 51 cm. In still other examples, the distance can be about 50 cm.

The low contrast letter acuity test module 52 can employ a front-facing camera (e.g., of a tablet computing device and/or a smartphone device) to ensure that the user is located at a desired range from the display device 28. A distance from the display is important, for example, for calculating a score for the LCLAT test. In some embodiments, distance can be measured with sensors incorporated into the computing device or added as peripherals. Such sensors may measure distance by, for example, light or sound. A score can be calculated based on the letters input by the user at a specific size and contrast. The low contrast letter acuity test module 52 can include an image processing function that can be related to the distance based on an image from the front-facing camera (e.g., log MAR scaling).

Additionally, traditional LCLAT tests can utilize bitmap images. In contrast, the LCLAT module 42 can utilize vector-type images to employ the LCLAT test. Advantageously, the vector-type images provide as an improvement over bitmap images with regard to the closer distance of users. Since the LCLAT test was originally designed for administration at 152 cm and is now, through the LCLAT module 42, administered at a shorter range, the vector-type images allow for a critical equivalence with resolution of images with 78% fewer pixels. This is because the vector type images enable appropriate scaling of the images to be viewable at shorter distances yet still appear the same to user.

The contrast sensitivity vision test module 54 can be used to administer a Contrast Sensitivity Vision Test. The contrast sensitivity vision test module 54 can provide an alternative method for measuring contrast sensitivity through the measurement of a Contrast Sensitivity Function (CSF). The measurement of the CSF can utilize wave-like gratings, for example sinusoidal gratings of varying spatial frequency and contrast levels that are rendered on the display that is spaced from the user's face by a determined distance. This assessment finds the threshold contrast at each spatial frequency, which is then fit to a truncated parabola, yielding the user's CSF. It has been determined that contrast is typically perceived in a parabolic fashion. As such, when plotting contrast vs. frequency, it is necessary to fit to a parabolic curve. This can be implemented programmatically, for example, through Matlab or similar systems.

In some examples, additional calibration can be employed to control the brightness of the display. For example, the module 54 (or another module) can control back light to a predetermined (e.g., maximum) brightness on the display. Ambient lighting may be measured and used to adjust the display in some examples (e.g., using average of pixel brightness from an optical sensor or camera). The display control further can be utilized to mitigate a bordering effect in the images acquired.

The contrast sensitivity vision test module 54 can, advantageously, measure the CSF of the user much faster than existing methods for measuring the CSF, which require expensive, specialized equipment, while lacking normative databases, longitudinal data and integration with other measures of function. These systems can allow for analysis, such as comparisons between user groups or across a single user's medical history (e.g., relative to one or more earlier tests and/or a baseline).

Figure 5:
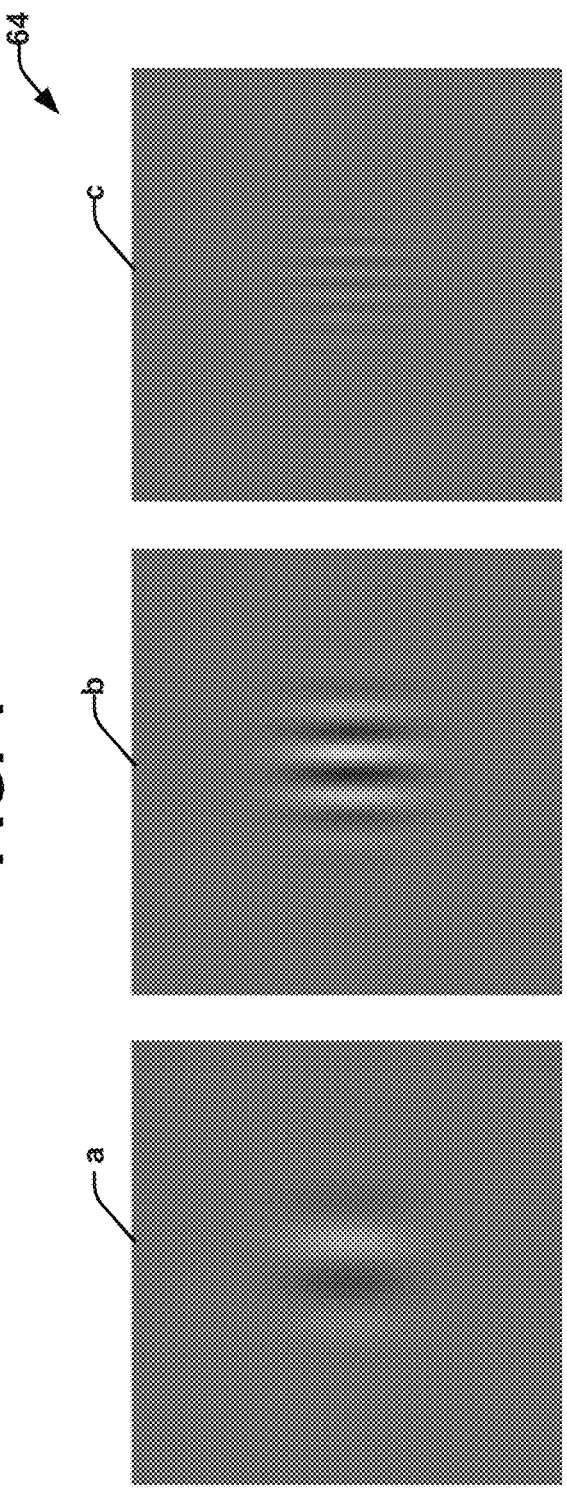

Example GUIs (64a-c) that can be produced by the contrast sensitivity vision test module 54 are shown in FIG. 5. The GUIs of the contrast sensitivity vision test module 54 can allow users to quickly measure their cutoff contrast at various spatial frequencies using a pseudo-random model. To produce the GUIs, the contrast sensitivity vision test module 54 can include a dithering function to produce the sine-wave gradient images of an equivalence of 31-bits of gray on an 8-bit system, for example. Other ranges of bits could be utilized to produce gradient images on given display. Additionally, the contrast sensitivity vision test module 54 can employ a data integrity algorithm to can check data validity in real time. Additionally, to calculate spatial frequency, the contrast sensitivity vision test module 54 can integrate the front-facing camera of the computing device 22 (e.g., a tablet computing device and/or a smartphone computing device) to determine a critical value for spatial frequency scaling. In other examples, a separate peripheral imaging device (e.g., digital camera) can be coupled to provide an image to the contrast sensitivity vision test module 54 for setting the spatial frequency scaling.

Figure 6:
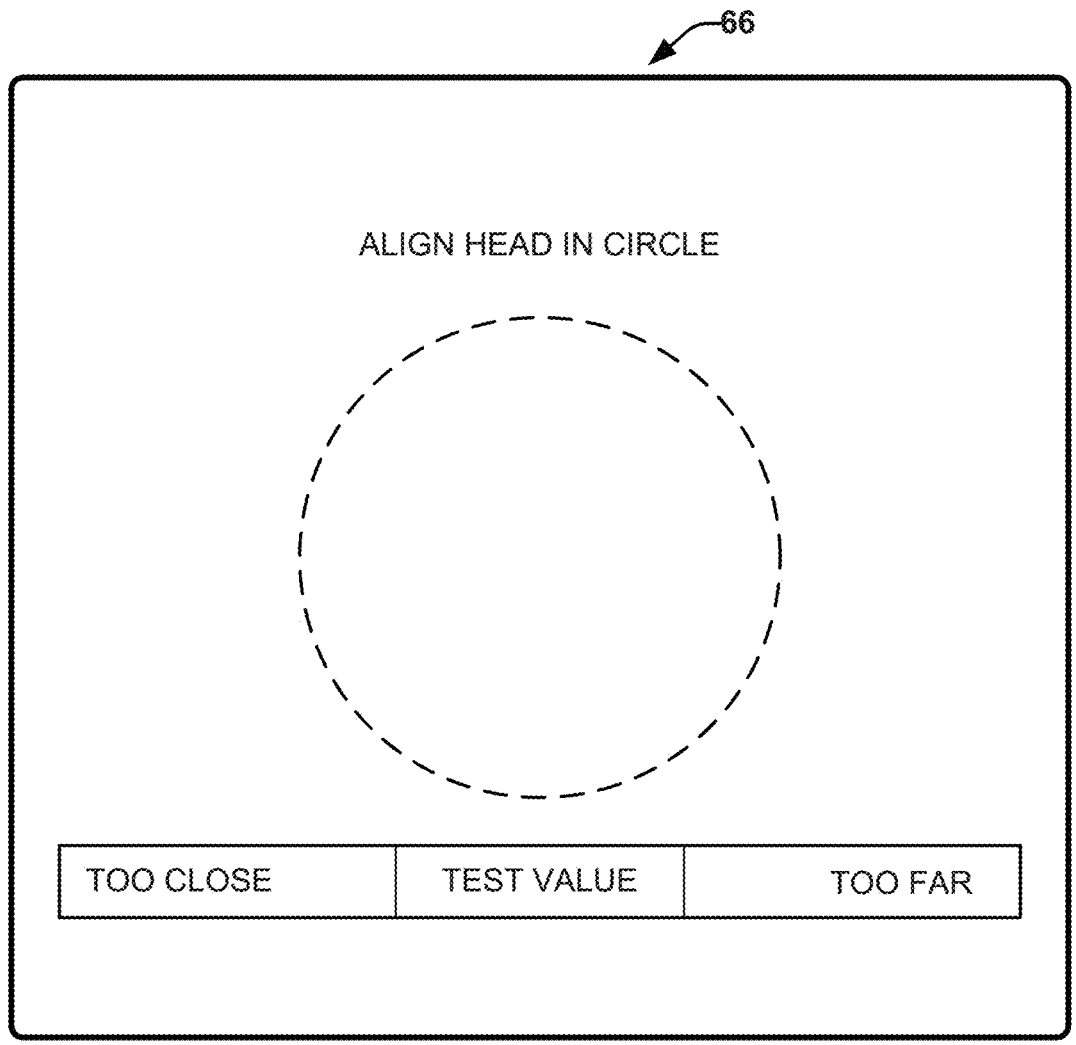
FIG. 6 depicts an example of a head alignment that is performed before conducting the automated low contrast visual acuity test.

FIG. 6 shows an example of how the front-facing camera can be used by the one or more of the test modules 50. As an example, the front facing camera can take an image of the user. The one or more test modules 50 can perform an alignment function (e.g., based on the presence of the user's head in an assigned location (e.g., within a circle, ellipse or other shaped graphics on the display). The assigned location can correspond to a distance of the user from the display device 38. The location can be used to calculate the score of the corresponding test module (e.g., LCLAT module 52 and/or CSVT module 54). For example, the score can be based on a number of correct user inputs at a specific size, contrast, letter, spacing, grayscale or color shading, etc.

Referring again to FIG. 3, a scoring module 54 can score results of the low contrast visual acuity test. For example, the score can be based on the display being presented by the test module 50 and the number of correct answers given by the user based on the display. The scoring module 54 can, in some examples, normalize the score for the test module 54 so that scores for different test modules can be compared.

The diagnostic module 56 can determine a medical status (e.g., a visual status) of the user based on the score. The medical status can be determined based on a comparison of scores, for example. In one example, the diagnostic module 56 can compare the score to previous scores for the user (e.g., an established baseline score for the user and the medical status either improves from the baseline or gets worse than the baseline). As an example, the baseline data can be recorded at a previous time (e.g., without the symptoms of the neurological disease and/or at a different stage of the neurological disease). The same tests can also be performed at another time, such as following an injury or other incident or occasion, such as for assessing a level of disease progress for the user. It will be understood that baseline data and historical data can be used interchangeably.

In another example, the diagnostic module 56 can compare the score for the user against a baseline reference score calculated from one or more historical subjects. The baseline reference score can be established based on data from one or more healthy users (e.g., an average value of data from a plurality of healthy users) representing hypothetical statistically normal user. The baseline reference can be based on user age, user gender, user weight, user height, and/or user fitness level. For example, a baseline reference for a 16 year old male football player can be different from the baseline reference for a 65 year old female with multiple sclerosis. The data may be compared against treatment regimens, such as drug treatments, eye exercises or glasses. In some examples, the baseline reference can be a constantly evolving group average. In other words, as more users contribute scores, the baseline reference changes. The changes can be constant, at certain predefined time points, or evolving after a certain number of patients contribute scores to the aggregate data set.

Figure 7:
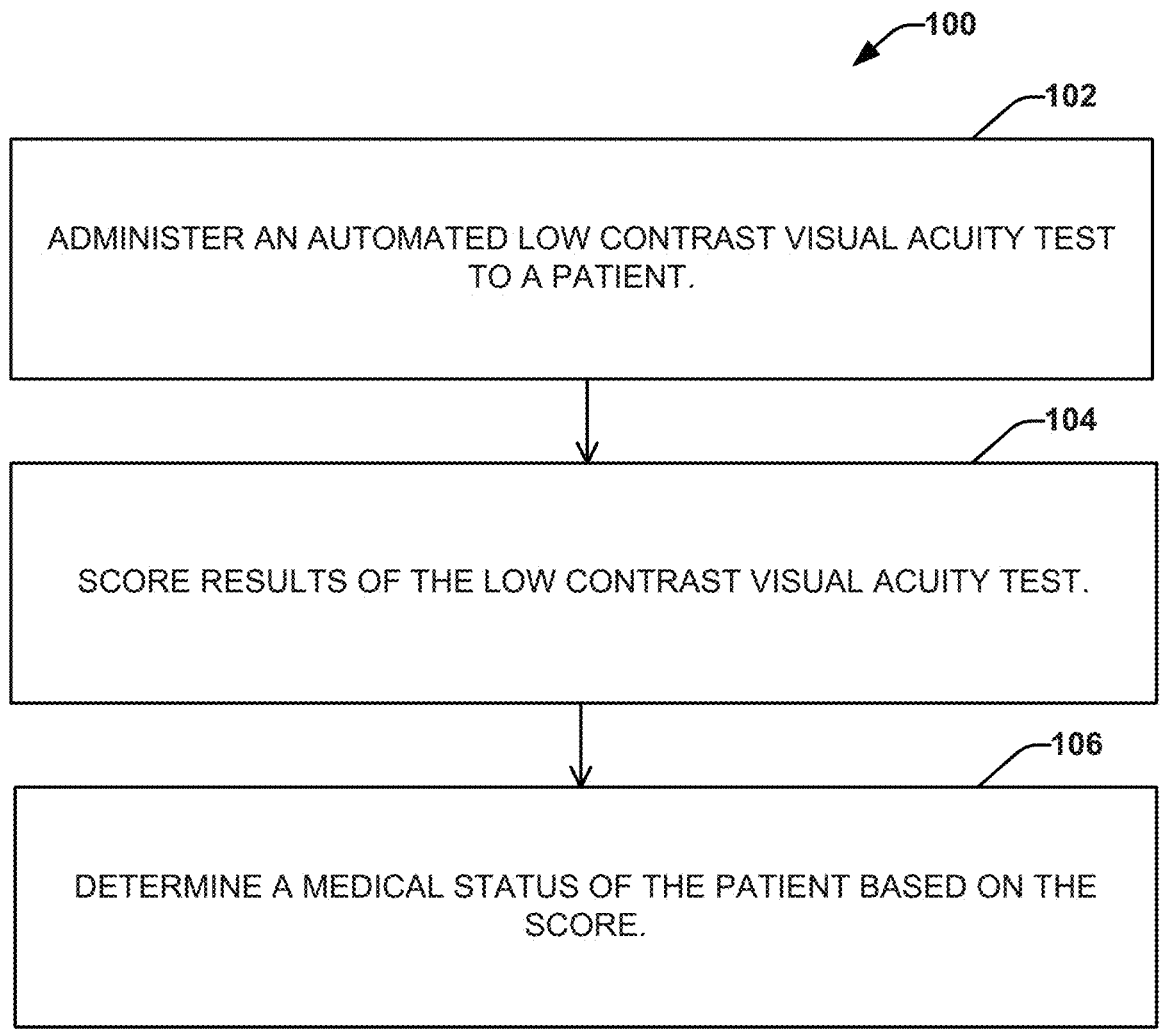
FIG. 7 depicts a process flow diagram of an example method for determining a disease state of a user based on an automated low contrast visual acuity test.
Figure 8:
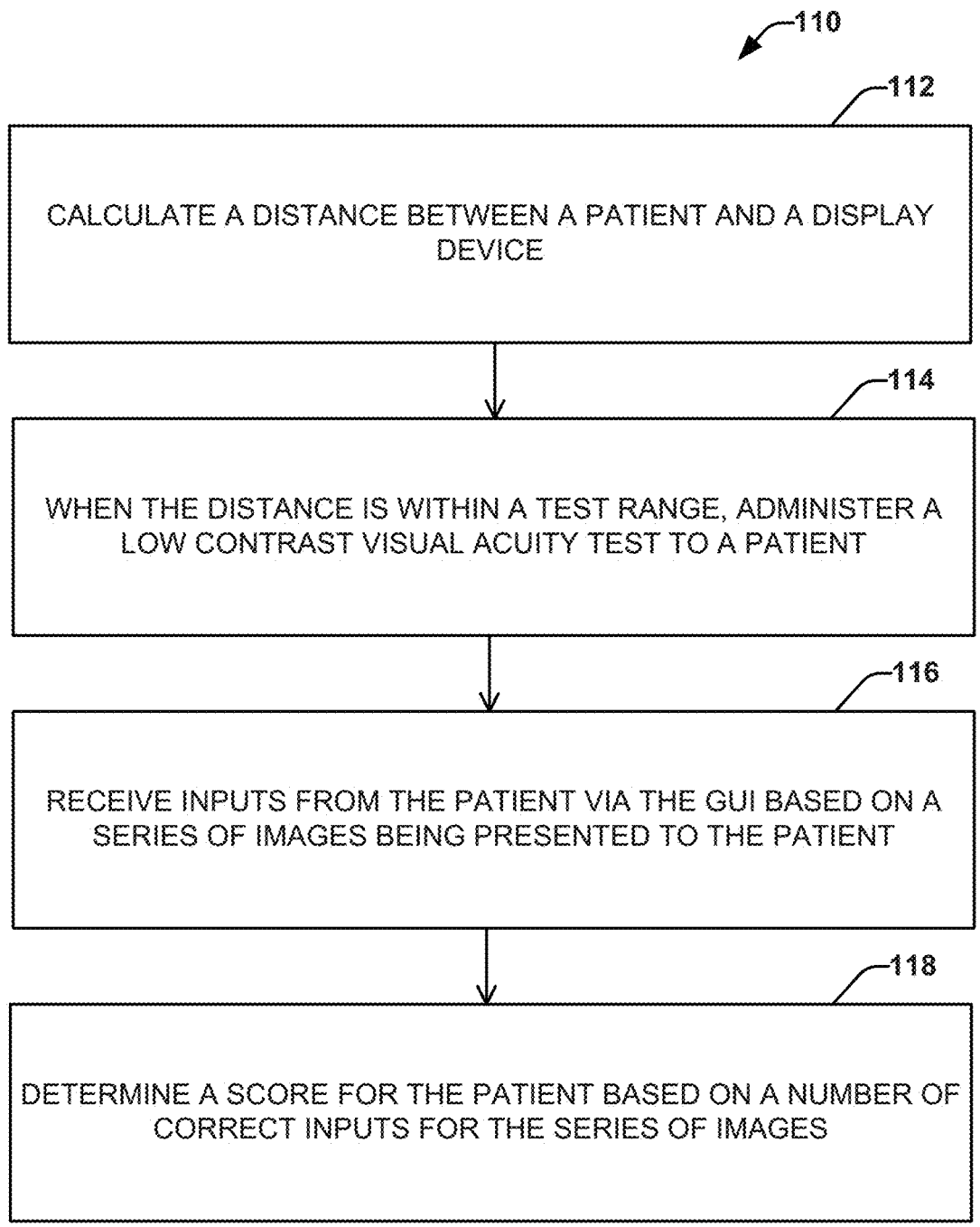
FIG. 8 depicts a process flow diagram of an example method for performing an automated low contrast visual acuity test.

In view of the foregoing structural and functional features described above, methods 100 and 110 in accordance with various aspects of the present invention will be better appreciated with reference to FIGS. 7 and 8. While, for purposes of simplicity of explanation, the methods 100 and 110 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect of the present invention. It will be appreciated that some or all of each of these methods can be implemented as machine-readable instructions on a non-transitory computer readable medium (e.g., memory 24).

FIG. 7 depicts a method 100 depicts an example of a method 100 for determining a disease state of a user based on an automated low contrast visual acuity test. The method 100 can be a computer implemented method. For example, method 100 can be stored on a non-transitory computer-readable medium and executed by a processor to cause a computing device (e.g., computing device 22) to perform operations of the method (as shown in acts 102-106).

At 102, an automated low contrast visual acuity test can be administered to a user (e.g., by computing device 22 using display device 38). For example, the low contrast visual acuity test can include one or more modules. The one or more modules can be retrieved from or executed on a server located within the cloud. The test for low contrast visual acuity can, for example, include modules for a LCLAT test and/or a CSVT test. For example, the LCLAT test can employ the GUI shown in FIG. 4 to facilitate the automated LCLAT test. In another example, the CSVT test can employ the GUI shown in FIG. 5 to facilitate the automated test of CSVT.

At 104, the results of the low contrast visual acuity test can be scored (e.g., by scoring module 54). For example, the scores can be normalized for the different tests to allow for comparison. At 108, a medical status (e.g., visual status) of the user can be determined based on the score (e.g., by diagnostic module 56).

FIG. 8 depicts a method 110 for administering an automated low contrast visual acuity test to a user. The method 110 can be a computer implemented method. For example, method 110 can be stored on a non-transitory computer-readable medium and executed by a processor to cause a computing device (e.g., computing device 22) to perform operations of the method (as shown in acts 112-116). Method 110 relies on at least one module related to the low contrast visual acuity test being launched and a corresponding GUI being displayed on a display device.

At 112, a distance between the display device and a user can be calculated based on data related to the distance measured by a sensor. At 114, when the distance between the display device and the user is within a test value (e.g., around 50 cm), the low contrast visual acuity test can be administered to the user. For example, the low contrast visual acuity test can be administered using the GUI by executing the at least one module to present a series of images to a user. At 116, inputs can be received from the user via the GUI based on the series of images being presented to the user. At 116, a score can be determined for the user based on a number of correct inputs for the series of images. Based on the score, a medical status (e.g., visual status) of the user can be determined.

Figure 9:
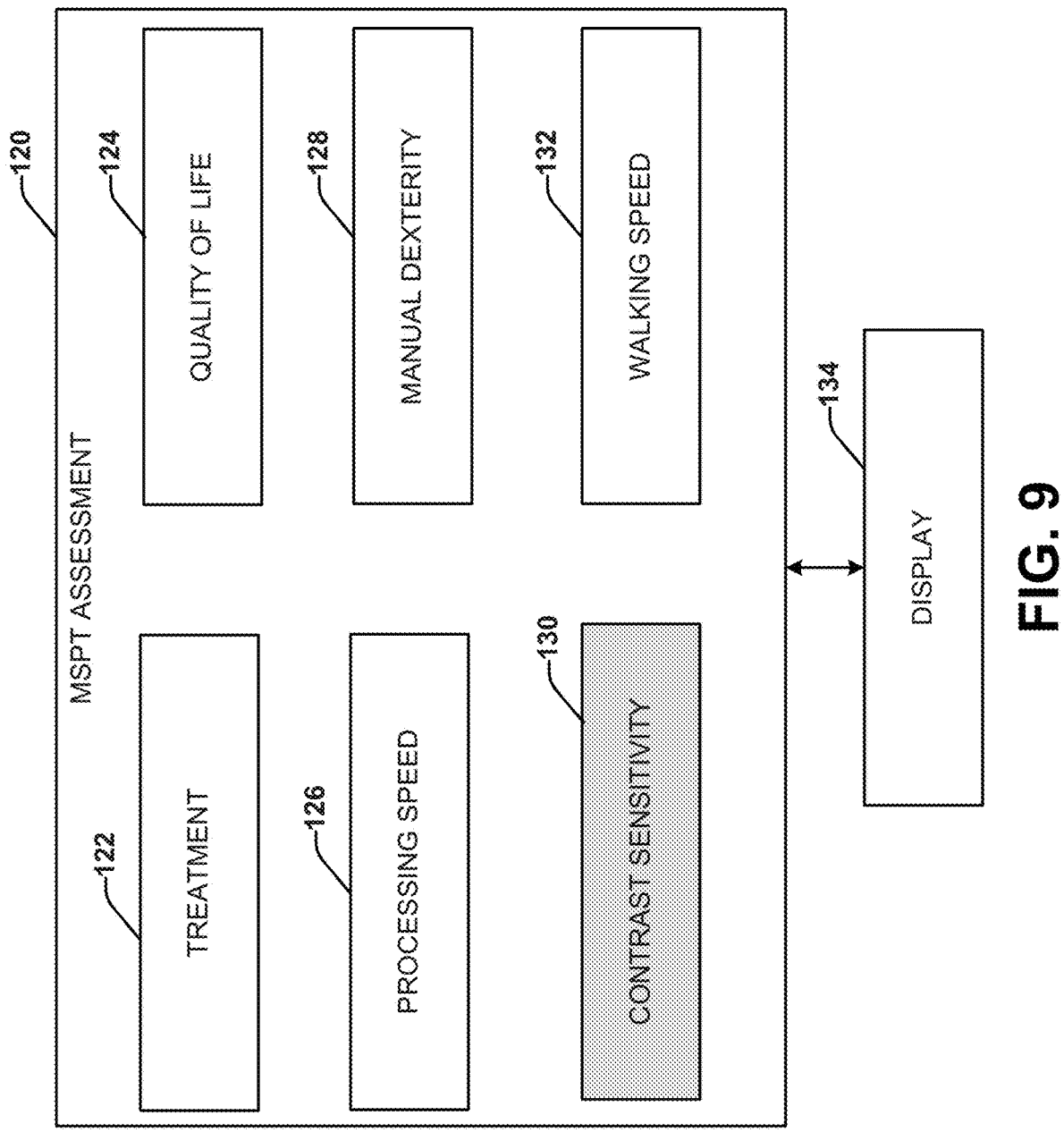
FIG. 9 depicts an example of different modules that can be part of a multiple sclerosis performance test (MSPT).

FIG. 9 shows an example of various modules of an example Multiple Sclerosis Performance Test (MSPT) assessment system 120. For example, the modules can include a treatment module 122, a quality of life module 124, a processing speed module 126, a manual dexterity module 128, a contrast sensitivity module 130 (e.g., applying the low contrast visual sensitivity test shown in FIGS. 1-8), and a walking speed module 132. Results of the MSPT can be visualized on the display 134. Additionally, aspects of each of the modules 122-130 can be displayed on the display 134 in a user-interactive manner. For example, the display 134 can be an input device, an output device, and/or an input/output device that can allow a user input and/or a resulting visualization. In some examples, the display can be part of a computing device that includes one or more processing unit and memory, which can execute instructions corresponding to the modules 122-130 and store data in the memory to document results of user interactions and measurements via the respective modules.

As can be appreciated by those skilled in the art, portions of the invention may be embodied as a method, data processing system, or computer program product (e.g., a non-transitory computer readable medium having instructions executable by a processor). Accordingly, these portions of the invention may take the form of an entirely hardware embodiment, an entirely software embodiment, or an embodiment combining software and hardware. Furthermore, portions of the invention may be a computer program product on a computer-usable storage medium having computer readable program code on the one or more media. Any suitable non-transitory computer-readable medium may be utilized including, but not limited to, static and dynamic storage devices, hard disks, optical storage devices, and magnetic storage devices.

Certain embodiments are disclosed herein with reference to flowchart illustrations of methods, systems, and computer program products. It can be understood that blocks of the illustrations, and combinations of blocks in the illustrations, can be implemented by computer-executable instructions. These computer-executable instructions may be provided to one or more processor cores of a general purpose computer, special purpose computer, or other programmable data processing apparatus (or a combination of devices and circuits) to produce a machine or a system that includes multiple machines, such that the instructions, which execute via the processor, implement the functions specified in the block or blocks.

These computer-executable instructions may also be stored in a non-transitory computer-readable medium that can direct a computer or other programmable data processing apparatus (e.g., one or more processing core) to function in a particular manner, such that the instructions stored in the computer-readable medium result in an article of manufacture including instructions which implement the function specified in the flowchart block or blocks. The computer program instructions may also be loaded onto one or more computers or other programmable data processing apparatus to cause a series of operational steps to be performed on the computer or other programmable apparatus to produce a computer implemented process such that the instructions which execute on the computer(s) or other programmable apparatus provide steps for implementing the functions specified in the flowchart block or blocks or the associated description.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system comprising:
a display device;
a sensor to measure a property related to a distance between the display device and a user;
a computing device comprising:
 a memory storing computer-executable instructions; and
 a processor to execute the computer-executable instructions to at least:
  launch at least one test module including a plurality of images related to a visual acuity test;
  display a graphical user interface (GUI) on the display device, wherein the GUI corresponds to the visual acuity test;
  conduct the visual acuity test by at least:
   calculating the distance between the display device and the user based on the property measured by the sensor;
   in response to determining that the calculated distance between the display device and the user is within a test value, presenting at least some of the plurality of images as a series of vector-type images that are scaled based on the calculated distance;
   detecting a change in the property measured by the sensor;
   calculating a new distance between the display device and the user based on the detected change in the property measured by the sensor; and
   in response to determining that the new distance between the display device and the user is within the test value, scaling the vector-type images based on the new distance;
  receive inputs from the user via the GUI based on the series of vector-type images being presented to the user as part of the visual acuity test;
  determine a score for the user based on the received inputs corresponding to answers to the visual acuity test; and
  determine a visual status of the user based on the determined score.

2. The system of claim 1, wherein the GUI comprises an on-screen keyboard that allows the user to self-administer the visual acuity test.

3. The system of claim 1, wherein the vector-type images comprise optotypes with varying at least one of contrasts, colors, shadings, and sizes.

4. The system of claim 1, wherein the test value is between 40 centimeters and 75 centimeters.

5. The system of claim 1, wherein the test value is between 48 centimeters and 55 centimeters.

6. The system of claim 1, wherein the sensor comprises a camera and the property related to the distance is determined based on image information from the camera.

7. The system of claim 1, wherein the visual status is determined based on comparing the determined score relative to at least one of a theoretical normal score, an average score corresponding to a user group, an evolving score corresponding to a user group or the user's historical scores.

8. The system of claim 1, wherein the visual acuity test is a low-contrast letter acuity test or a contrast sensitivity vision test.

9. A method comprising:

launching, by a computing device comprising a processor, at least one test module including a plurality of images related to a visual acuity test;

displaying, by the computing device, a graphical user interface (GUI) on a display device, wherein the GUI corresponds to the visual acuity test;

conducting, by the computing device, the visual acuity test by at least:

calculating a distance between the display device and a user based on data describing a property related to a distance measured by a sensor;

when the distance between the display device and the user is within a test value, presenting at least some of the plurality of images as a series of vector-type images that are scaled based on the calculated distance;

detecting a change in the property measured by the sensor;

calculating a new distance between the display device and the user based on the detected change in the property measured by the sensor; and when the new distance between the display device and the user is within the test value, scaling the vector-type images being presented based on the calculated new distance;

receiving, by the computing device, inputs from the user via the GUI based on the series of vector-type images being presented to the user as part of the visual acuity test;

determining, by the computing device, a score for the user based on the received inputs corresponding to answers to the visual acuity test; and determining, by the computing device, a visual status of the user based on the score.

10. The method of claim 9, further comprising retrieving, by the computing device, the at least one test module from a remote server.

11. The method of claim 9, wherein the test value is between 40 centimeters and 75 centimeters.

12. The method of claim 9, wherein the test value is between 48 centimeters and 55 centimeters.

13. The method of claim 9, wherein the visual status is determined based on comparing the determined score relative to at least one of a theoretical normal score, an average score corresponding to a user group, an evolving score corresponding to a user group, or the user's historical scores.

14. The method of claim 9, wherein the visual acuity test includes at least one of a low contrast letter acuity test or a contrast sensitivity vision test.

15. The method of claim 9, wherein the GUI comprises an on-screen keyboard that allows the user to self-administer the visual acuity test.

16. The method of claim 9, wherein the vector-type images comprise optotypes of varying at least one of contrasts, colors, shadings, and sizes.

17. The method of claim 9, further comprising sending, by the computing device, at least one of the score and the visual status to a remote device for further analysis by an expert.

18. The method of claim 9, wherein the computing device is a smartphone, a tablet computer or a laptop computer.

19. The method of claim 18, wherein the computing device includes the sensor and the display device.

20. The method of claim 9, wherein the at least one test module is related to a low contrast visual acuity test or a contrast sensitivity vision test.

* * * * *